(12) United States Patent
Murakami et al.

(10) Patent No.: US 7,501,409 B2
(45) Date of Patent: Mar. 10, 2009

(54) PREPARATIONS FOR ORAL ADMINISTRATION

(75) Inventors: Hideki Murakami, Kobe (JP); Shoji Takebe, Takatsuki (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 606 days.

(21) Appl. No.: 10/363,322

(22) PCT Filed: Sep. 6, 2001

(86) PCT No.: PCT/JP01/07718

§ 371 (c)(1),
(2), (4) Date: Mar. 3, 2003

(87) PCT Pub. No.: WO02/20058

PCT Pub. Date: Mar. 14, 2002

(65) Prior Publication Data

US 2003/0195220 A1    Oct. 16, 2003

(30) Foreign Application Priority Data

Sep. 6, 2000 (JP) ............... 2000-270061
Jul. 31, 2001 (JP) ............... 2001-231682

(51) Int. Cl.
*C07D 241/10*    (2006.01)
*A61K 31/56*    (2006.01)

(52) U.S. Cl. .................... 514/231.5; 514/182

(58) Field of Classification Search ........ 424/400, 424/464, 484; 514/252.1, 256, 231.5, 258
See application file for complete search history.

(56) References Cited

U.S. PATENT DOCUMENTS

| | | | |
|---|---|---|---|
| 5,721,238 A | 2/1998 | Heiker et al. | |
| 5,861,396 A | 1/1999 | Niewohner et al. | |
| 5,861,404 A | 1/1999 | Niewohner et al. | |
| 5,866,571 A | 2/1999 | Niewohner et al. | |
| 5,902,824 A | 5/1999 | Ulrich | |
| 5,981,527 A | 11/1999 | Daugan et al. | |
| 6,018,046 A | 1/2000 | Ohashi et al. | |
| 6,069,156 A | 5/2000 | Oku et al. | |
| 6,080,782 A | 6/2000 | Ulrich et al. | |
| 6,127,378 A | 10/2000 | Gutterer | |
| 6,140,329 A | 10/2000 | Daugan | |
| 6,191,138 B1 | 2/2001 | Gutterer | |
| 6,548,490 B1 * | 4/2003 | Doherty et al. | 514/182 |
| 6,797,709 B2 * | 9/2004 | Yamada et al. | 514/231.5 |
| 2002/0037828 A1 * | 3/2002 | Wilson et al. | 514/1 |

FOREIGN PATENT DOCUMENTS

| | | |
|---|---|---|
| EP | 960621 A2 | 12/1999 |
| EP | 0 995 750 A1 | 4/2000 |
| EP | 0 995 751 A2 | 4/2000 |
| EP | 1 120 120 A1 | 8/2001 |
| EP | 1 142 880 A1 | 10/2001 |
| EP | 1 219 609 A1 | 7/2002 |
| JP | 10-298062 A | 11/1998 |
| JP | 10-240446 A | 3/2000 |
| JP | 2000-72675 A | 3/2000 |
| JP | 2000-72751 A | 3/2000 |
| JP | 2000-95759 A | 4/2000 |
| WO | WO 94/28902 A1 | 12/1994 |
| WO | WO 96/16657 A1 | 6/1996 |
| WO | WO 98/30209 A1 | 7/1998 |
| WO | WO 98/38168 A1 | 9/1998 |
| WO | WO 00/20033 A1 | 4/2000 |
| WO | WO 00/24383 A1 | 5/2000 |
| WO | WO 00/32195 A1 | 6/2000 |
| WO | WO 01/19802 A1 | 3/2001 |
| WO | WO 01/27105 A1 | 4/2001 |

* cited by examiner

*Primary Examiner*—Michael G Hartley
*Assistant Examiner*—Jagadishwar R Samala
(74) *Attorney, Agent, or Firm*—Birch, Stewart, Kolasch & Birch, LLP

(57) ABSTRACT

The present invention provides a preparation for oral administration containing a medicinal substance having cGMP-specific phosphodiesterase inhibitory activity and showing decrease of solubility in the neutral and alkaline regions, wherein an acidic substance is compounded promote the dissolution of the medicinal substance in digestive tract and thus the efficacy can be expressed at the early stage after administration, and which preparation is useful in treatment of erectile dysfunction.

10 Claims, 2 Drawing Sheets

PREPARATIONS FOR ORAL ADMINISTRATION

TECHNICAL FIELD

The present invention relates to a preparation for oral administration, which contains a cGMP-specific phosphodiesterase inhibitor and has an improved capacity of expressing the drug efficacy. More specifically, the present invention related to an oral preparation containing a medicinal substance having cGMP-specific phosphodiesterase inhibitory activity and showing decrease of solubility in the neutral and alkaline regions, which preparation is compounded with an acidic substance and thereby being capable of expressing the drug efficacy rapidly after oral administration.

BACKGROUND ART

Latent patients with erectile dysfunction increases as the population ages and, considering the advent of an aging society in near future, attention has been concentrated on the significance of improving the quality of life (QOL) of patients by treatment. As a therapeutic agent, a cyclic GMP (cGMP)-specific phosphodiesterase (PDE) inhibitor, especially PDE-V inhibitor is used.

A therapeutic agent for erectile dysfunction preferably exerts the drug efficacy immediately after taking the agent so that the sexual response can be regulated on demand. However, some PDE-V inhibitors are known to show marked decrease in solubility in the neutral and alkaline regions compared to the acidic region. For example, the solubility of sildenafil citrate is 2.52 mg/ml at pH 1.2, while it is only 0.11 mg/ml at pH 6.8 (WO00/20033, page 4).

Thus, such a PDE-V inhibitor, when administered to a subject who just finished eating or is suffering from anacidity, would not dissolve well in the digestive tract, resulting in the delay of expression of efficacy and/or reduction of bioavailability (BA). For example, even Viagra (Pfizer) which is a rapid-acting tablets of sildenafil citrate, it has been reported that one should take the preparation about 1 hour in advance of the time when the efficacy is expected to be expressed (WO00/24383, page 2).

Examples of known PDE-V inhibitor-containing preparations for oral administration include intraoral quickly disintegrating tablets (JP-A 10-298062) prepared by a process comprising subjecting a mixture containing sildenafil citrate and a bondable disintegrant to wet granulation followed by compression molding, and granules coated with flavor mask (WO98/30209) wherein a core containing sildenafil citrate is coated with an inner coating layer of hydroxypropylcellulose and an outer coating layer of Eudragit-E 100 (gastric-soluble polymer). However, these preparations are directed to the improvement of disintegration of tablets or masking of bitterness and is irrelevant to the improvement of the solubility of PDE-V inhibitor itself.

There are also described tablets immediately disintegrating in the oral cavity (WO00/20033) wherein the solubility of PDE-V inhibitor is improved, which have been prepared by mixing a PDE-V inhibitor (sildenafil, phthaladine derivatives, etc.) with sugars, kneading together with a solvent and compressing under pressure. However, the preparations do not show sufficiently accelerated expression of drug efficacy as expected.

DISCLOSURE OF INVENTION

In view of the above-mentioned background, the present inventors have intensively studied for the purpose of developing a novel preparation which contains as an active ingredient a cGMP PDE inhibitor showing decrease of solubility in the neutral and alkaline ranges, and which can achieve rapid expression of efficacy of the active ingredient even when the preparation is administered to a subject who is suffering from anacidity or who intends to take the same just after eating, and established the present invention.

The present invention provides a novel preparation for oral administration containing as an active ingredient a cGMP PDE inhibitor showing decrease of solubility in the neutral and alkaline regions, which preparation is compounded with an acidic substance and, if necessary, a carbonate and thereby can exert drug efficacy rapidly after administration.

BEST MODE FOR CARRYING OUT THE INVENTION

Figure 1:
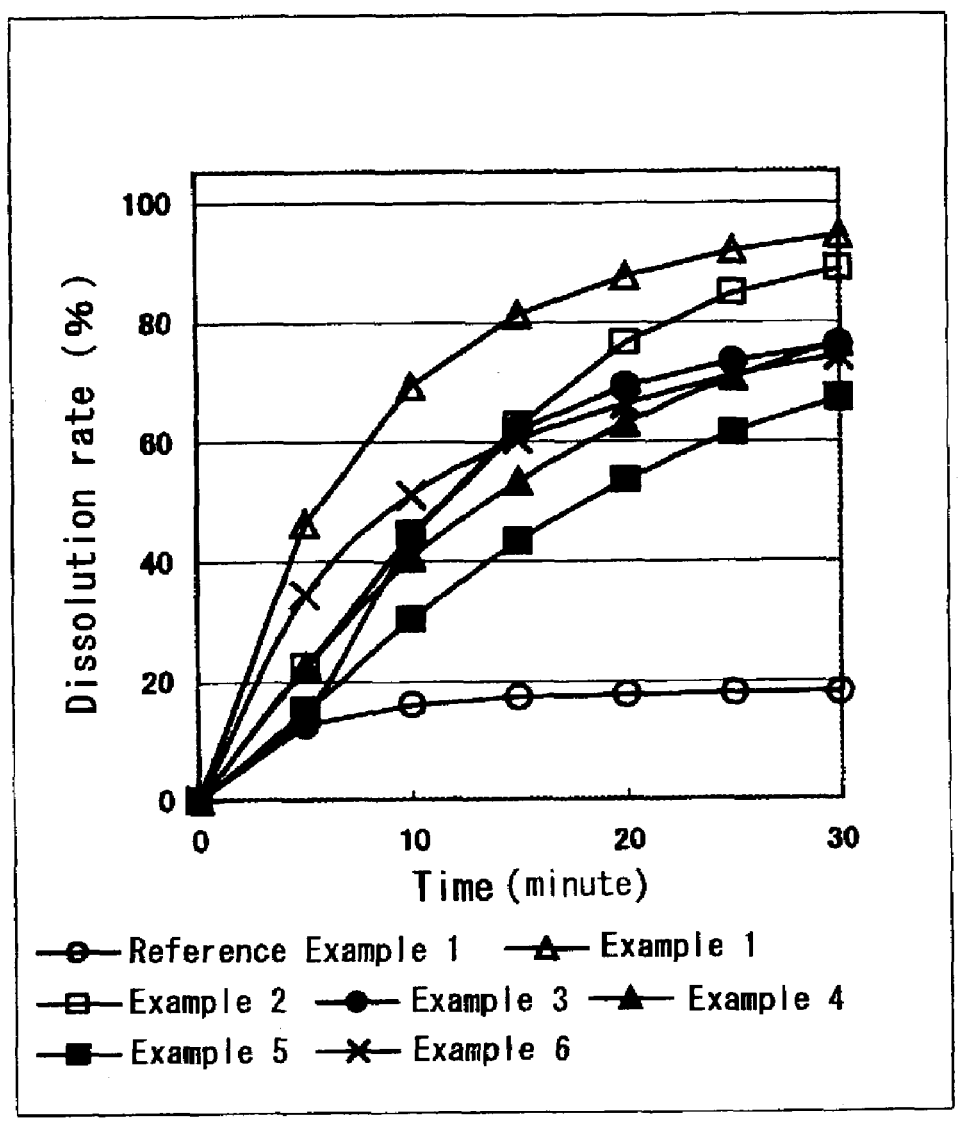
FIG. 1 is a graph showing the results of dissolution test conducted using the preparations of Examples 1-6 and Reference Example 1.

Examples of the medicinal substance usable as an active ingredient of the preparation for oral administration of the present invention include any substances which have a cGMP-specific phosphodiesterase inhibitory activity (hereinafter, referred to as "PDE-V inhibitor"), and which show decrease in solubility in the neutral and alkaline regions. The phrase "neutral and alkaline regions" refers to a region of pH 4 or above, generally, to the range of pH 5-pH 10 and the phrase "decrease in solubility in the neutral and alkaline regions" means that, for example, the solubility of a substance at pH 6.8 is ¹/₁₀ or less, preferably ¹/₁₅ or less, more preferably ¹/₂₀ or less compared to the solubility at pH 1.2. Specific examples of such PDE-V inhibitors include those described in Japanese Patent Translation Publication Hei-9-512835 and Hei-9-503996, JP-A-2000-128883, JP-A-2000-128884, Japanese Patent Translation Publications Hei-11-505236, Hei-11-505539, 2000-507256 and 2000-503996, JP-A-2000-95759, JP-A-10-298164, JP-A-2000-72675, JP-A-2000-72751, JP-A-9-124648, JP-A-8-231545, JP-A-8-231546, JP-A-8-253457, Japanese Patent Translation Publication Hei-11-503445, WO97/45427, Japanese Patent Translation Publications Hei-11-509221, Hei-11-509517 and Hei-11-509535, WO00/20033, WO00/39099, WO01/19802, and the like.

Preferred PDE-V inhibitors include an aromatic nitrogen-containing 6-membered cyclic compound of the formula (I):

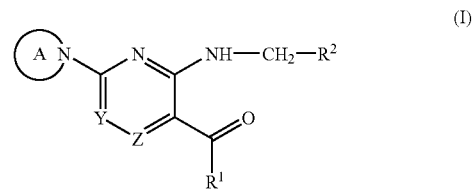

wherein ring A is an optionally substituted nitrogen-containing heterocyclic group; $R^1$ is an optionally substituted lower alkyl group, a group of the formula: —NH-Q-$R^3$ (wherein $R^3$ is an optionally substituted nitrogen-containing heterocyclic group, and Q is a lower alkylene group or a single bond), or a group of the formula: —NH—R⁴ (wherein R⁴ is an optionally substituted cycloalkyl group); R² is an optionally substituted aryl group; one of Y and Z is a group of the formula: =CH—, and the other is a group of the formula: =N—, or a pharmaceutically acceptable salt thereof. See, WO01/19802.

Examples of the nitrogen-containing heterocyclic group of the "optionally substituted nitrogen-containing heterocyclic group" for Ring A include a 5- to 10-membered monocyclic or bicyclic nitrogen-containing heterocyclic group, more particularly, a 5- or 6-membered nitrogen-containing heteromonocyclic group and a 8- to 10-membered nitrogen-containing heterobicyclic group, and most particularly, a 5- or 6-membered non-aromatic nitrogen-containing heteromonocyclic group such as pyrrolidinyl group, piperazinyl group, piperidyl group, a nitrogen-containing heterobicyclic group wherein any one of above-mentioned 5- or 6-membered non-aromatic nitrogen-containing heteromonocyclic group is condensed with a 5- or 6-membered aromatic nitrogen-containing heteromonocyclic group such as 1H-2,3-dihydropyrroro[3,4-b]pyridin-2-yl group, 5,6,7,8-tetrahydroimidazo[1,2-a]pyrazin-7-yl group, 5,6,7,8-tetrahydro-1,7-naphthyridin-7-yl group, and the like.

Examples of the nitrogen-containing heterocyclic group of the "optionally substituted nitrogen-containing heterocyclic group" for R³ include a 5- or 6-membered nitrogen-containing heteromonocyclic group, for example, a 5- or 6-membered non-aromatic nitrogen-containing heteromonocyclic group such as morpholinyl group, a 5- or 6-membered aromatic nitrogen-containing heteromonocyclic group such as pyrimidinyl group, pyridazinyl group, pyridyl group, and the like.

Examples of the substituent of the "optionally substituted nitrogen-containing heterocyclic group" for Ring A and R³ include a lower alkyl group, a hydroxy-substituted lower alkyl group, a formyl group, an oxo group, and the like.

Examples of the aryl group of the "optionally substituted aryl group" for R² include a 5- to 10-membered monocyclic or bicyclic aromatic hydrocarbon group such as phenyl group, naphthyl group and the like.

Examples of the substituent of the "optionally substituted aryl group" for R² include a lower alkoxy group, a halogen atom, a cyano group, and the like.

Examples of the substituent of the "optionally substituted lower alkyl group" for R¹ and the substituent of the "optionally substituted cycloalkyl group" for R⁴ include a lower alkoxy group, a hydroxy group, a morpholinyl group, and the like.

Throughout the present description and the claims, the term "lower alkyl group" means a straight chain or branched chain alkyl group having 1 to 6 carbon atoms, such as methyl, ethyl, propyl, isopropyl, butyl, isobutyl, tert-butyl, etc. The term "lower alkoxy group" means a straight chain or branched chain alkoxy group having 1 to 6 carbon atoms, such as methoxy, ethoxy, propoxy, isopropyloxy, butyloxy, isobutyloxy, tert-butyloxy, etc. The term "cycloalkyl group" means a cycloalkyl group having 3 to 8 carbon atoms, such as cyclopropyl, cyclobutyl, cyclopentyl, cyclohexyl, cycloheptyl, etc. The term "lower alkylene group" means a straight chain or branched chain alkylene group having 1 to 6 carbon atoms, such as methylene, ethylene, trimethylene, etc.

The present oral preparation is also applicable to a compound in the free form. Accordingly, a compound which shows disadvantages regarding stability, operationality, etc. in the form of acid addition salt can be conveniently used in the present preparation.

Specific Examples of the PDE-V inhibitor usable in the present invention include the following compounds.

(S)-2-(2-Hydroxymethyl-1-pyrrolidinyl)-4-(3-chloro-4-methoxybenzylamino)-5-[N-(2-pyrimidinylmethyl)carbamoyl]pyrimidine 2-(5,6,7,8-Tetrahydroimidazo[1,2-a]pyrazin-7-yl)-4-(3-chloro-4-methoxybenzylamino)-5-[N-(2-pyrimidinylmethyl)carbamoyl]pyrimidine 2-(5,6,7,8-Tetrahydro-1,7-naphthyridin-7-yl)-4-(3-chloro-4-methoxybenzylamino)-5-[N-(2-morpholinoethyl)carbamoyl]pyrimidine (S)-2-(2-Hydroxymethyl-1-pyrrolidinyl)-4-(3-chloro-4-methoxybenzylamino)-5-[N-(5-pyrimidinylmethyl)carbamoyl]pyrimidine (S)-2-(2-Hydroxymethyl-1-pyrrolidinyl)-4-(3-chloro-4-methoxybenzylamino)-5-[N-(1,3,5-trimethyl-4-pyrazolyl)carbamoyl]pyrimidine A medicinal substance is compounded in a pharmaceutically effective amount which varies depending on the kind of medicinal substance; however, it is generally in the range of 0.1-99 weight %, preferably 1-50 weight % on the basis of the total weight of the preparation.

Examples of the acidic substance that can be used in the present oral preparation include any substance on condition that it shows pH 4.0 or below when dissolved in water and does not interfere with the efficacy of a medicinal substance as an active ingredient, and preferred examples include an organic acid such as fumaric acid, tartaric acid, succinic acid, malic acid, ascorbic acid, aspartic acid, and the like. These organic acids can be used alone or in combination of two or more acids. Especially preferable acidic substance is fumaric acid.

The preferred ratio of a medicinal substance and an acidic substance in the present preparation somewhat differs depending on the kinds of the medicinal substance and/or the acidic substance, but the ratio (medicinal substance: acidic substance) is usually in the range of 1:0.05 to 1:30, preferably 1:0.25 to 1:3. The ratio of an acidic substance will be elevated when the medicinal substance is in the free form than when it is in a salt form such as acid addition salt.

In addition to the above-mentioned acidic substance, a carbonate may also be compounded in the present oral preparation, which possibly leads to the further improvement of dissolution of a medicinal substance in the digestive tract, the enhancement of the moldability when tableting and the increase of the productivity.

Examples of the carbonate available include alkali metal carbonate such as sodium carbonate, etc., alkali metal hydrogen carbonate such as sodium hydrogen carbonate, etc., alkali earth metal carbonate such as calcium carbonate, magnesium carbonate, etc., and they can be used alone or in combination of two or more. Among these carbonates, calcium carbonate is especially preferred.

A carbonate can be compounded in amount of not greater than 10%, preferably 5%, especially preferably 3% by weight, based on the total amount of the preparation.

The present oral preparation may contain additives generally used in the pharmaceutical solid preparations. Examples of the additives include excipients such as lactose, sucrose, mannitol, xylitol, erythritol, sorbitol, maltitol, calcium citrate, calcium phosphate, crystalline cellulose and calcium aluminometasilicate, etc.; disintegrants such as corn starch, potato starch, sodium carboxymethyl starch, partially pregelatinized starch, calcium carboxymethylcellulose, carboxymethylcellulose, low-substituted hydroxypropylcellulose, cross-linked sodium carboxymethylcellulose, cross-linked polyvinylpyrrolidone, etc.; binders such as hydroxypropylcellulose, hydroxypropylmethylcellulose, polyvinylpyrrolidone, polyethyleneglycol, dextrin, pregelatinized starch, etc.;

lubricants such as magnesium stearate, calcium stearate, talc, light anhydrous silicic acid, anhydrous silica dioxide, etc,; surfactants such as phospholipid, glycerin fatty acid ester, sorbitan fatty acid ester, polyoxyethylene fatty acid ester, polyethylene glycol fatty acid ester, polyoxyethylene hydrogenated castor oil, polyoxyethylene alkyl ether, sucrose fatty acid ester, etc.; flavors such as orange oil, fennel oil, cinnamon oil, clove oil, turpentine oil, peppermint oil, eucalyptus oil, etc.; colorants such as Food Color Red Nos. 2 and 3, Food Color Yellow Nos. 4 and 5, Food Color Green No. 3, Food Color Blue Nos. 1 and 2, and aluminum lakes of these Food Colors, iron sesquioxide, yellow iron sesquioxide, etc.; sweetenings such as saccharine, aspartame, etc.; solubilizing agents such as dicyclodextrin, arginine, lysine, trisaminomethane, etc., and the like.

The present preparation for oral administration can be in the form of ordinary solid pharmaceutical preparations such as powders, granules, tablets, capsules, etc. The tablets are preferred considering the productivity, convenience of administration, masking effect on bitter taste, and the like, and especially tablets comprising a medicinal substance and an acidic substance separately in respective granules are preferred. These solid preparations may be coated with sugar coating or film coating with the aim of, for example, preventing abrasion wear, masking bitterness, improving stability; however, they are preferably uncoated to avoid adverse influence on the dissolution of an active ingredient, if there are no particular inconveniences.

The solid pharmaceutical preparation of the present invention contains a medicinal substance having cGMP phosphodiesterase-inhibitory activity and is applicable to prevention and treatment of penile erectile dysfunction, pulmonary hypertension, gastroparesis diabeticorum, hypertension, angina pectoris, myocardial infarction, chronic and acute heart failure, female sexual dysfunction, prostatic hyperplasia, asthma, diarrhea, constipation, achalasia, etc., and is particularly useful in prevention and treatment of penile erectile dysfunction.

Specific examples of oral preparation of the present invention include those comprising the following constituents.

(1) Tablets comprising (S)-2-(2-hydroxymethyl-1-pyrrolidinyl)-4-(3-chloro-4-methoxybenzylamino)-5-[N-(2-pyrimidinylmethyl)carbamoyl]pyrimidine and fumaric acid;
(2) Tablets comprising (S)-2-(2-hydroxymethyl-1-pyrrolidinyl)-4-(3-chloro-4-methoxybenzylamino)-5-[N-(2-pyrimidinylmethyl)carbamoyl]pyrimidine, fumaric acid and calcium carbonate;
(3) Tablets comprising 2-(5,6,7,8-tetrahydro-1,7-naphthyridin-7-yl)-4-(3-chloro-4-methoxybenzylamino)-5-[N-(2-molpholinoethyl)carbamoyl]pyrimidine and fumaric acid;
(4) Tablets comprising 2-(5,6,7,8-tetrahydro-1,7-naphthyridin-7-yl)-4-(3-chloro-4-methoxybenzylamino)-5-[N-(2-molpholinoethyl)carbamoyl]pyrimidine, fumaric acid and calcium carbonate;
(5) Tablets comprising (S)-2-(2-hydroxymethyl-1-pyrrolidinyl)-4-(3-chloro-4-methoxybenzylamino)-5-[N-(1,3,5-trimethyl-4-pyrazolyl)carbamoyl]pyrimidine and fumaric acid;
(6) Tablets comprising (S)-2-(2-hydroxymethyl-1-pyrrolidinyl)-4-(3-chloro-4-methoxybenzylamino)-5-[N-(1,3,5-trimethyl-4-pyrazolyl)carbamoyl]pyrimidine, fumaric acid and calcium carbonate.

The oral preparation of the present invention can be prepared in accordance with a conventional method for preparing pharmaceutical solid formulations.

Powders can be prepared by compounding a medicinal substance with an acidic substance and optionally calcium carbonate, and, if necessary, further a pharmaceutically acceptable additive(s), and mixing in a conventional manner.

Granules can be prepared by any one of known methods for preparing granules such as wet granulation, dry granulation, layering granulation, melt-granulation, impregnated-granulation, etc. The outline of respective granulation methods is described below.

(i) Wet Granulation

A drug mixture is prepared by mixing a medicinal substance, an acidic substance, and, if necessary, a carbonate and a pharmaceutical additive(s). The drug mixture is combined with an aqueous solution of a binder and subjected to stirring and granulation with a mixer granulator or a high-shear mixer granulator, etc. In alternative process, the drug mixture is combined with an aqueous solution of a binder, kneaded, and subjected to granulation and sizing with an extrusion granulator. In still alternative process, an aqueous solution of a binder is sprayed the drug mixture under fluid condition with a fluidized bed granulator, a tumbling mixer fluidized bed granulator, etc.

(ii) Dry Granulation

A drug mixture is prepared, as mentioned above, by mixing a medicinal substance, an acidic substance, and, if necessary, a carbonate and a pharmaceutical additive(s), and subjected to granulation with a roller compactor, a roll granulator, etc.

(iii) Layering Granulation

A drug mixture similar to the above is added to an rolling inactive carriers while spraying an aqueous binder solution with a centrifugal fluidized bed granulator or the like to make the drug mixture adhere to the carries. Examples of the inactive carrier that used in this method include crystals of sugars or inorganic salts such as crystalline lactose, crystalline cellulose, crystalline sodium chloride, etc., and spherical granules such as spherical granules of crystalline cellulose (brand name: Avicel SP, Asahi Kasei Corporation), spherical granules of crystalline cellulose and lactose (brand name: Nonpareil-NP-5 and NP-7, Freund Co., Ltd.), spherical granules of purified white sugar (brand name: Nonpareil-103, Freund Co., Ltd.), spherical granules of lactose and α starch, etc.

(iv) Melt-granulation

A drug mixture containing a melting material, which melts under heating, is prepared by mixing a medicinal substance, an acidic substance and, if necessary, a carbonate and a pharmaceutical additive(s) to a melting material such as polyethylene glycol, fat, wax, etc. The resulting drug mixture is subjected to stirring and granulation with a mixer granulator or a high-shear mixer granulator, etc. at temperature under which the melting material melts. Alternatively, a drug mixture containing a melting material as mentioned above is added to rolling inactive carriers at temperature under which the melting material melts with a centrifugal fluidized bed granulator, whereby making the drug mixture adhere to the carries, The same inactive carriers as mentioned above can be used.

(v) Impregnating Granulation

A drug solution containing a medicinal substance, an acidic substance and the like at an appropriate concentration is mixed with porous carriers thereby a sufficient amount of drug solution is made to retain in the cavities of the carrier, which is followed by drying to remove the solvent. Examples of the porous carrier that can be used include magnesium aluminometasilicate (bland name: Neusiline, Fuji Chemical Industry Co., Ltd.), calcium silicate (Florite, Eisai Co., Ltd.), etc. Examples of the solvent in which a medicinal substance, an acidic substance, etc. are dissolved include water, ethanol, methanol, or the like.

Tablets can be manufactured by either subjecting a drug mixture prepared in the same manner as above to the compression molding as it is, or subjecting said drug mixture to the granulation as mentioned above, and then to the compression molding after adding a disintegrant(s), lubricant(s), etc., if needed. If a carbonate is compounded, it is preferably added at the same time when a disintegrant, a lubricant, etc. are added. If desired, an additional acidic substance(s) can be compounded.

Further, in the process wherein a drug mixture is granulated, a drug mixture containing a medicinal substance and a pharmaceutical additive(s) without an acidic substance can be granulated. The resulting granules are then mixed with an acidic substance and, if necessary, a carbonate, a disintegrant and a lubricant, and then subjected to compression molding. In this process, granules of an acidic substance prepared by the granulation method above can be used, whereby tablets comprising different granules each containing a medicinal substance and an acidic substance separately are prepared.

The compression molding can be conducted using a conventional tableting machine such as rotary tableting machine, single punch tableting machine, dual tableting machine, and the like, with a compressing pressure of generally about 50 to 4,000 kg/cm².

The capsules can be manufactured by filling in hard capsules either a drug mixture obtained by mixing a medicinal substance, an acidic substance and, if necessary, a carbonate and a pharmaceutical additive(s) as it is, or in the form of powders, granules or tablets prepared in a manner as described above.

Various preparations that can be obtained according to the manufacturing methods above can be coated with sugar coating or film coating for the purpose of preventing abrasion wear, masking bitterness, improving stability, and the like. The coating can be carried out in a conventional manner; however, it is preferable to confine the coating amount to such an extent that does not disturb the dissolution of a medicinal substance.

A compound (I), which is a preferred PDE-V inhibitor for the present invention, can be prepared by reacting a compound of the formula (II):

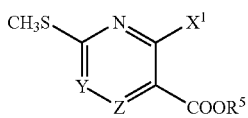
(II)

wherein $X^1$ is a halogen atom, $R^5$ is a protecting group for the carboxyl group and the other symbols are the same as defined above with a compound of the formula (III):

(III)

wherein the symbol is the same as defined above;
oxidizing the resulting compound of the formula (IV):

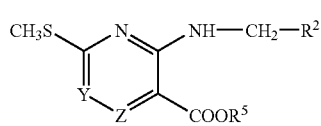
(IV)

wherein the symbols are the same as defined above to give a methylsulfonyl (or methylsulfinyl) compound of the formula (V):

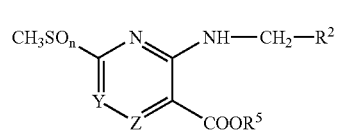
(V)

wherein n is 1 or 2 and the other symbols are the same as defined above;
reacting the compound (V) with a compound of the formula (VI):

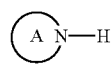
(VI)

wherein the symbol is the same as defined above, or a salt thereof to give a compound of the formula (VII):

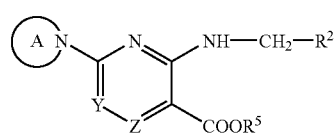
(VII)

wherein the symbols are the same as defined above;
removing the protecting group $R^5$ for the carboxyl group to give a compound of the formula (VIII):

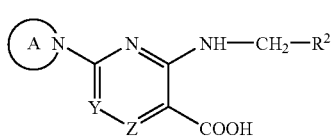
(VIII)

wherein the symbols are the same as defined above; and
reacting the compound (VIII) with a compound of the formula (IX-a):

(IX-a)

wherein $R^{11}$ is a group of the formula —NH-Q-$R^3$ or —NH—$R^4$.

The compound (I) can also be prepared by halogenating a compound (VIII) to give a compound of the formula (X):

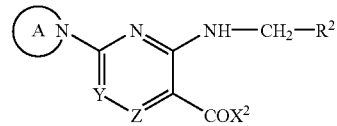
(X)

wherein $X^2$ is a halogen atom and the other symbols are the same as defined above, and reacting the compound (X) with a compound of the formula (IX-a).

The compound (VII) above can also be prepared by treating a dihalogeno compound of the formula (XI):

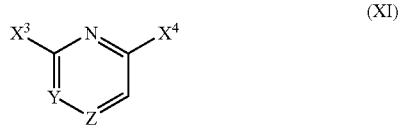

wherein $X^3$ is a halogen atom, $X^4$ is a halogen atom and the other symbols are the same as defined above with a carbon dioxide to give a compound of the formula (XII):

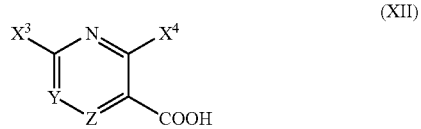

wherein the symbols are the same as defined above; protecting the carboxyl group of the compound (XII) to give a compound of the formula (XIII):

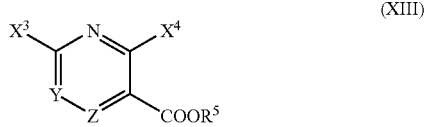

wherein the symbols are the same as defined above; reacting the compound (XIII) with a compound of the formula (III) to give a compound of the formula (XIV):

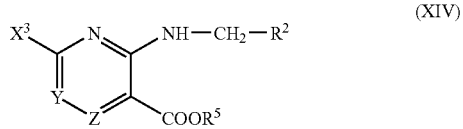

wherein the symbols are the same as defined above; and reacting the compound (XIV) with a compound (VI).

The compound (XIV) above can also be prepared by hydrolyzing a compound (V) to give a compound of the formula (XV):

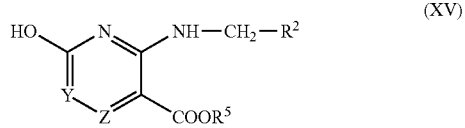

wherein the symbols are the same as defined above; and halogenating the compound (XV).

The above processes can be carried out as follows.

The reaction of the compound (II) with the compound (III) is carried out in the presence or absence of an acid scavenger in a solvent. The acid scavenger includes, for example, an organic base such as N,N-diisopropylethylamine, N-methylmorpholine, triethylamine, pyridine, etc., and an inorganic base such as sodium hydride, sodium carbonate, potassium carbonate, sodium hydrogen carbonate, etc. The solvent may be any solvent which does not disturb the reaction, for example, dimethylformamide, tetrahydrofuran, toluene, ethyl acetate, chloroform, dimethoxyethane, xylene, dimethylsulfoxide, etc. The reaction is carried out at a temperature of −10° C. to room temperature, preferably 0° C. to room temperature.

The reaction for oxidizing the compound (IV) to give the methylsulfonyl (or methylsulfinyl) compound (V) is carried out in the presence of an oxidizing agent in a solvent. The oxidizing agent includes, for example, peracids such as m-chloroperbenzoic acid, peracetic acid, etc., and inorganic oxidizing agents such as manganese dioxide, sodium periodate, hydrogen peroxide, acyl nitrate, dinitrogen tetroxide, halogen, N-halide, hydroperoxide, iodobenzene acetate, t-butyl hypochlorite, sulfuryl chloride, potassium peroxymonosulfate (oxone), etc. The solvent may be any solvent which does not disturb the reaction, for example, chloroform, methylene chloride, dichloroethane, acetic acid, etc. The reaction is carried out at a temperature of −78° C. to 50° C., preferably −10° C. to 10° C.

The reaction of the compound (V) with the compound (VI) or a salt thereof can be carried out in the presence or absence of an acid scavenger in a solvent. The acid scavenger includes, for example, an organic base such as N,N-diisopropylethylamine, N-methylmorpholine, triethylamine, pyridine, etc., and an inorganic base such as sodium hydride, sodium carbonate, potassium carbonate, sodium hydrogen carbonate, etc. The salt of the compound (VI) is preferably an alkali metal salt such as sodium salt, potassium salt, etc. The solvent may be any solvent which does not disturb the reaction, for example, dimethylformamide, tetrahydrofuran, dimethoxyethane, dimethylsulfoxide, etc. The reaction is carried out at a temperature of 0° C. to 150° C., preferably room temperature to 60° C.

The reaction of removing the protecting group $R^5$ for the carboxyl group of the compound (VII) to give the compound (VIII) can be carried out by a conventional method such as hydrolysis, catalytic reduction, etc. depending on the type of the carboxyl protecting group. When a protecting group for carboxyl group is removed by hydrolysis, the hydrolysis can be carried out, for example, in the presence of a base in a solvent. The base is preferably, for example, an alkali metal hydroxide such as sodium hydroxide, potassium hydroxide, lithium hydroxide, etc., or an alkali metal carbonate such as sodium carbonate, potassium carbonate, etc. The solvent may be water or a mixture of water and methanol, ethanol, tetrahydrofuran, dioxane, dimethylformamide, dimethylsulfoxide, etc. The reaction is carried out at a temperature of 0 to 80° C., preferably 5° C. to 60° C. The protecting group for carboxyl group represented by $R^5$ may be any groups conventionally used for protecting a carboxyl group, such as a lower alkyl group, benzyl group, etc.

The reaction of the compound (VIII) with the compound (IX-a) can be carried out in the presence or absence of a condensing agent, a base or an activator in a suitable solvent. The condensing agent includes, for example, dicyclohexylcarbodiimide, 1-ethyl-3-(3-dimethylaminopropyl)carbodiimide, diphenylphosphoryl azide, diethylcyanophosphonate, etc., which is commonly used in the peptide synthesis. The base includes, for example, an organic base such as triethylamine, N-methymorpholine, etc., and the activator includes, for example, 1-hydroxybenzotriazole, etc. The solvent may be any solvent which does not disturb the reaction, for example, methylene chloride, tetrahydrofuran, dimethylformamide, acetonitrile, dimethylacetamide, ethyl acetate, etc. The present reaction proceeds preferably in the presence of an activator or a base. The activator includes hydroxybenzotriazole, etc. and the base include triethylamine, N-methymorpholine, etc. The reaction is carried out at a temperature of −30° C. to 50° C., preferably −10° C. to 10° C.

The alternative process wherein the compound (VIII) is converted into the compound (X) which is further reacted with the compound (IX-a) can be carried out by firstly reacting the compound (VIII) with a halogenating agent in the presence or absence of an activator by a conventional method, and reacting the resulting compound (X) with the compound (IX-a). The reaction of the compound (VIII) with a halogenating agent can be carried out in a solvent. The halogenating agent is preferably, for example, thionyl chloride, oxalyl chloride, phosphorus pentachloride, etc. The activator is preferably, for example, an amide compound such as dimethylformamide, etc. The solvent may be any solvent which does not disturb the reaction, for example, methylene chloride, chloroform, tetrahydrofuran, benzene, toluene, dioxane, etc. The reaction is carried out at a temperature of −30° C. to 100° C., preferably −5° C. to 10° C.

The subsequent reaction with the compound (IX-a) can be carried out in the presence of an acid scavenger in a solvent. The acid scavenger includes, for example, an organic base such as N,N-diisopropylethylamine, N-methylmorpholine, triethylamine, pyridine, dimethylaminopyridine, etc., and an inorganic base such as sodium hydride, sodium carbonate, potassium carbonate, sodium hydrogen carbonate, etc. The solvent may be any solvent which does not disturb the reaction, for example, tetrahydrofuran, methylene chloride, chloroform, toluene, benzene, dioxane, ethyl acetate, etc. The reaction is carried out at a temperature of −30° C. to 100° C., preferably −5° C. to 10° C.

The reaction of treating the dihalogeno compound (XI) with carbon dioxide to give the compound (XII) can be carried out in the presence of a base in a solvent. The base includes, for example, an alkali metal salt of an organic base such as lithium diisopropylamide, lithium 2,2,6,6-tetramethylpiperidide, etc. The solvent may be any solvent which does not disturb the reaction, for example, tetrahydrofuran, 1,2-dimethoxyethane, diethyl ether, etc. The reaction is carried out at a temperature of −100° C. to −30° C., preferably −100° C. to −70° C.

The reaction of protecting the carboxyl group of the compound (XII) to give the compound (XIII) can be carried out by a conventional method, for example, by reacting with an alkylating agent in the presence of a base in a solvent, when the protecting group is a lower alkyl group. The alkylating agent is preferably a lower alkyl halide such as methyl iodide. The base is preferably an alkali metal hydrogen carbonate such as sodium hydrogen carbonate, and the solvent may be any solvent which does not disturb the reaction, for example, dimethylformamide, tetrahydrofuran, etc. The reaction is carried out at a temperature of 0° C. to 100° C., preferably room temperature to 70° C.

The reaction of the compound (XIII) with the compound (III) to give the compound (XIV) can be carried out in the same manner as in the reaction of the compound (II) with the compound (III).

The reaction of the compound (XIV) with the compound (VI) to give the compound (VII) can be carried out in the same manner as in the reaction of the compound (V) with the compound (VI).

The hydrolysis reaction of the compound (V) to give the compound (XV) can be carried out in the presence of a base in a solvent. The base includes, for example, an alkali metal hydroxide such as sodium hydroxide, potassium hydroxide, lithium hydroxide, etc., and an alkali metal carbonate such as sodium carbonate, potassium carbonate, etc. The solvent is preferably water, or a mixture of water and methanol, ethanol, tetrahydrofuran, dioxane, dimethylformamide, dimethylsulfoxide, etc. The reaction is carried out at a temperature of −20° C. to 80° C., preferably −5° C. to 60° C.

The reaction of halogenating the compound (XV) to give the compound (XIV) can be carried out in the same manner as in the reaction wherein the compound (X) is obtained by halogenating the compound (XIII) by a halogenating agent.

EXAMPLE 1

A 25 weight % aqueous hydroxypropylcellulose (HPC-SL, Nippon Soda Co., Ltd.) solution (70 g) is added to (S)-2-(2-hydroxymethyl-1-pyrrolidinyl)-4-(3-chloro-4-methoxybenzylamino)-5-[N-(2-pyrimidinylmethyl)-carbamoyl]pyrimidine (i.e., a PDE-V inhibitor) (250 g), mannitol (325 g) and fumaric acid (100 g), and mixed for granulation with a planetary mixer (5DMV-01-r, Dalton, Co., Ltd.). The granules are dried, sized with a sizer (P-02S, Dalton Co., Ltd.) and sieved through a No. 22 Sieve. To an aliquot (650 g) of the resultant granules are added low-substituted hydroxypropylcellulose (L-HPC, Shin-Etsu Chemical Co., Ltd.) (41.9 g) and magnesium stearate (7.0 g), and mixed with a double cone mixer (Yashima Chemical Engineering Co., Ltd.) at 55 rpm for 3 minutes to yield granules for tableting. The granules are compressed with a rotary tableting machine (CPC818 HUK-DC-AWC, Kikusui Seisakusyo Ltd., punch: 7.5 φ, 11R, compressing pressure: 6 kN/punch) to yield tablets containing PDE-V inhibitor (150 mg/tablet).

EXAMPLE 2

Tablets containing PDE-V inhibitor are prepared in the same manner as described in Example 1 except that tartaric acid is used instead of fumaric acid.

EXAMPLE 3

Tablets containing PDE-V inhibitor are prepared in the same manner as described in Example 1 except that succinic acid is used instead of fumaric acid.

EXAMPLE 4

Tablets containing PDE-V inhibitor are prepared in the same manner as described in Example 1 except that malic acid is used instead of fumaric acid.

EXAMPLE 5

Tablets containing PDE-V inhibitor are prepared in the same manner as described in Example 1 except that ascorbic acid is used instead of fumaric acid.

EXAMPLE 6

Tablets containing PDE-V inhibitor are prepared in the same manner as described in Example 1 except that aspartic acid is used instead of fumaric acid.

EXAMPLE 7

(1) The same mixture as described in Example 1, which comprises PDE-V inhibitor (250 g), mannitol (325 g) and fumaric acid (100 g) is sprayed (15 g/minutes) with an 8 weight % aqueous hydroxypropylcellulose (HPC-SL, Nippon Soda Co., Ltd.) solution (281.3 g) under fluidized condition while keeping the in-take air temperature at 50° C. by means of a fluidized bed granulator (Type MP-01, Powrex Corporation). After completion of spray, the products are fluidized and dried until the product temperature becomes 45° C. while keeping the intake-air temperature at 60° C.

(2) To an aliquot (650 g) of the resultant granules are added low-substituted hydroxypropylcellulose (L-HPC, Shin-Etsu Chemical Co., Ltd.) (41.9 g) and magnesium stearate (7.0 g), and mixed with a double cone mixer (Yashima Chemical Engineering Co., Ltd.) at 55 rpm for 3 minutes to yield granules for tableting. The granules are compressed with a rotary tableting machine (CPC818 HUK-DC-AWC, Kikusui Seisakusyo Ltd., punch: 7.5 φ, 11R, compressing pressure: 6 kN/punch) to yield tablets containing PDE-V inhibitor (150 mg/tablet).

EXAMPLE 8

Granules are prepared in the same manner as described in Example 7 (1). To an aliquot (650 g) of the resultant granules are added low-substituted hydroxypropylcellulose (L-HPC, Shin-Etsu Chemical Co., Ltd.) (41.9 g), magnesium stearate (7.0 g) and precipitated calcium carbonate (7.0 g), and mixed with a double cone mixer (Yashima Chemical Engineering Co., Ltd.) at 55 rpm for 3 minutes to yield granules for tableting. The granules are compressed with a rotary tableting machine (CPC818 HUK-DC-AWC, Kikusui Seisakusyo Ltd., punch: 7.5 φ, 11R, compressing pressure: 6 kN/punch) to yield tablets containing PDE-V inhibitor (151.5 mg/tablet).

EXAMPLE 9

Granules obtained in the same manner as described in Example 7(1) except that 2-(5,6,7,8-tetrahydroimidazo[1,2-a]pyrazin-7-yl)-4-(3-chloro-4-methoxybenzylamino)-5-[N-(2-pyrimidinylmethyl)carbamoyl]pyrimidine is used as a PDE-V inhibitor are treated in the same manner as described in Example 8 to yield tablets containing PDE-V inhibitor.

EXAMPLE 10

Granules obtained in the same manner as described in Example 7(1) except that 2-(5,6,7,8-tetrahydro-1,7-naphthyridin-7-yl)-4-(3-chloro-4-methoxybenzylamino)-5-[N-(5-pyrimidinylmethyl)carbamoyl]pyrimidine is used as a PDE-V inhibitor are treated in the same manner as described in Example 8 to yield tablets containing PDE-V inhibitor.

EXAMPLE 11

Granules obtained in the same manner as described in Example 7(1) except that (S)-2-(2-hydroxymethyl-1-pyrrolidinyl)-4-(3-chloro-4-methoxybenzylamino)-5-[N-(5-pyrimidinylmethyl)carbamoyl]pyrimidine is used as a PDE-V inhibitor are treated in the same manner as described in Example 8 to yield tablets containing PDE-V inhibitor.

EXAMPLE 12

Granules obtained in the same manner as described in Example 7(1) except that (S)-2-(2-hydroxymethyl-1-pyrrolidinyl)-4-(3-chloro-4-methoxybenzylamino)-5-[N-(1,3,5-trimethyl-4-pyrazolyl)carbamoyl]pyrimidine is used as a PDE-V inhibitor are treated in the same manner as described in Example 8 to yield tablets containing PDE-V inhibitor.

EXAMPLE 13

(1) The same mixture as described in Example 1, which comprises PDE-V inhibitor (2450 g) an mannitol (3077.2 g), is sprayed (60 g/minutes) with an 8 weight % aqueous hydroxypropylcellulose (HPC-SL, Nippon Soda Co., Ltd.) solution (2450 g) under fluidized condition while keeping the in-take air temperature at 60° C. by means of a fluidized bed granulator (Type MP-01, Powrex Corporation). After completion of spray, the products are fluidized and dried until the product temperature becomes 45° C. to yield PDE-V inhibitor granules.

(2) Separately, fumaric acid (6000 g) is sprayed (40 g/minutes) with an 8 weight % aqueous hydroxypropylcellulose (HPC-SL, Nippon Soda Co., Ltd.) solution (1875 g) under fluidized condition while keeping the in-take air temperature at 60° C. by means of a fluidized bed granulator (Type MP-01, Powrex Corporation). After completion of spray, the products are fluidized and dried until the product temperature becomes 45° C. to yield fumaric acid granules.

(3) PDE-V inhibitor granules (5548 g) and fumaric acid granules (973.8 g) are taken from the respective granules obtained in the above, combined with low-substituted hydroxypropylcellulose (L-HPC, Shin-Etsu Chemical Co., Ltd.) (427.5 g) and precipitated calcium carbonate (71.3 g), and subjected to mixing with a double cone mixer (Tokuju Corporation) at 30 rpm for 10 minutes. After addition of magnesium stearate (104.5 g), the mixing is continued with a double cone mixer (Tokuju Corporation) at 30 rpm for 3 minutes to yield granules for tableting. The granules are compressed with a rotary tableting machine (CPC818 HUK-DC-AWC, Kikusui Seisakusyo Ltd., punch: 7.5 φ, 11R, compressing pressure: 6 kN/punch) to yield tablets containing PDE-V inhibitor (150 mg/tablet).

REFERENCE EXAMPLE 1

To a mixture similar to that described in Example 1, i.e., PDE-V inhibitor (250 g) and mannitol (425 g), a 25 weight % aqueous hydroxypropylcellulose (HPC-SL, Nippon Soda Co., Ltd.) solution (70 g) is added, and the mixture is mixed for granulation with a planetary mixer (5DMV-01-r, Dalton, Co., Ltd.). The granules are dried, sized with a sizer (P-02S, Dalton CO., Ltd.) and sieved through a No. 22 Sieve. To an aliquot (650 g) of the resultant granules are added low-substituted hydroxypropylcellulose (L-HPC, Shin-Etsu Chemical Co., Ltd.) (41.9 g) and magnesium stearate (7.0 g), and mixed with a double cone mixer (Yashima Chemical Engineering Co., Ltd.) at 55 rpm for 3 minutes to yield granules for tableting. The granules are compressed with a rotary tableting machine (CPC818 HUK-DC-AWC, manufactured by Kikusui Seisakusyo Ltd., punch: 7.5 φ, 11R, compressing pressure: 6 kN/punch) to yield tablets containing PDE-V inhibitor (150 mg/tablet).

Experiment 1

The tablets prepared in Examples 1-6 and Reference Example 1 were subjected to the dissolution test in accordance with the teaching of the Japanese Pharmacopoeia 14th Edition (puddle method, 50 r.p.m., test solution: water, wave length of measurement: 295, 450 nm). The results are shown in FIG. 1.

As shown in FIG. 1, the tablets of Examples 1-6, to which an acidic substance has been added, show greatly improved dissolution rate of a medicinal substance compared to the preparation of Reference Example 1 which does not contain an acidic substance.

Experiment 2

The tablets prepared in Examples 7 and 8 were subjected to the dissolution test in accordance with the teaching of the Japanese Pharmacopoeia 14th Edition (puddle method, 50 r.p.m., test solution: water, wave length of measurement: 295, 450 nm. The results are shown in FIG. 2.

Figure 2:
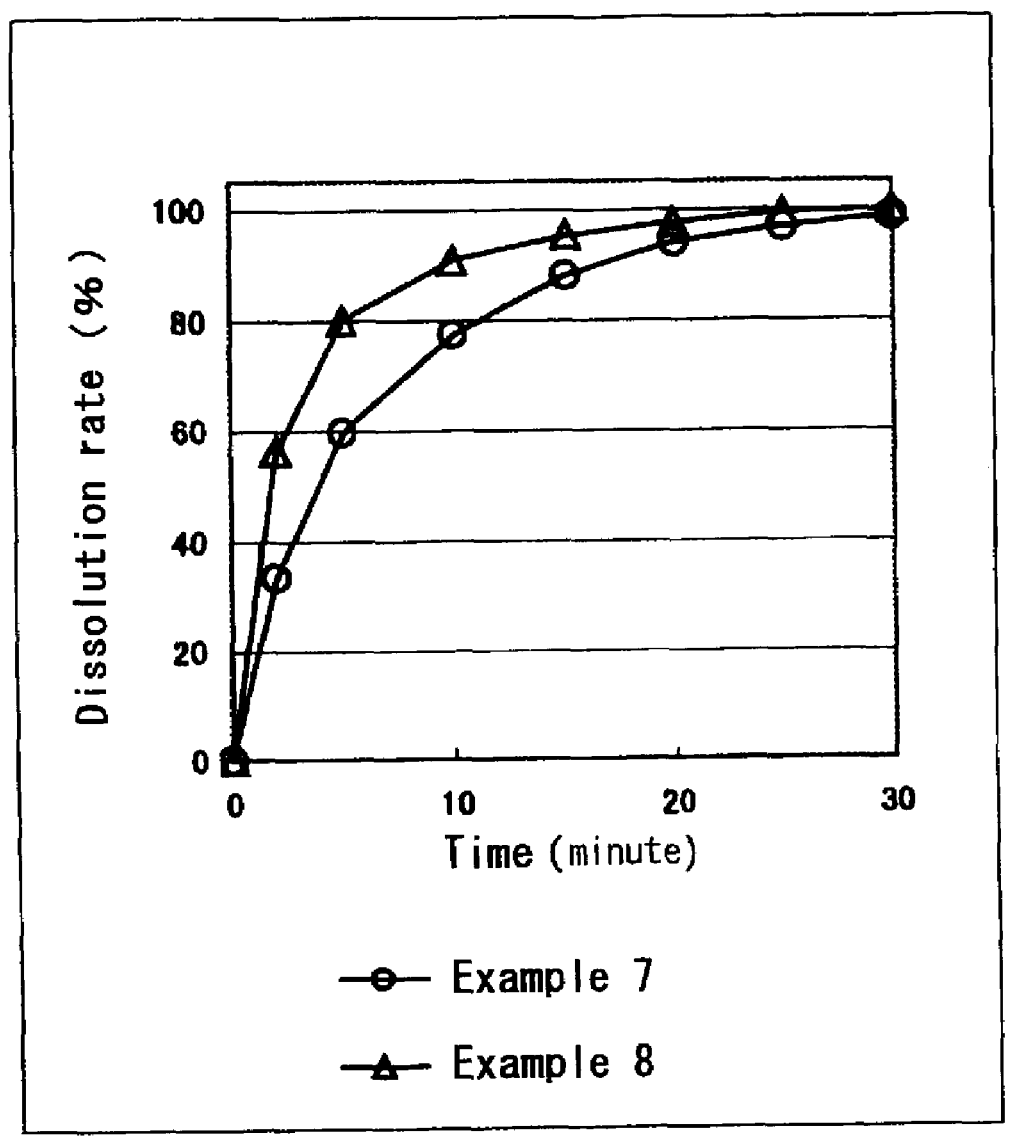
FIG. 2 is a graph showing the results of dissolution test conducted using the preparations of Examples 7 and 8.

As shown in FIG. 2, the dissolution rate of a medicinal substance was further improved by adding precipitated calcium carbonate in addition to an organic acid.

Preparation 1

(1) To a solution of 4-chloro-5-ethoxycarbonyl-2-methylthiopyrimidine (25.33 g) in N,N-dimethylformamide (85 ml) are added a solution of 3-chloro-4-methoxybenzylamine (19.62 g) in N,N-dimethylformamide (15 ml) and triethylamine (16.7 ml) under ice-cooling. The mixture is stirred at room temperature for 20 minutes, and thereto is added 3-chloro-4-methoxybenzylamine (940 mg), and the mixture is further stirred for 15 minutes. To the mixture is further added said amine (940 mg), and the mixture is stirred for 15 minutes. The reaction mixture is poured into a mixture of ice water and citric acid, and extracted with ethyl acetate. The extract is washed successively with a 10% aqueous citric acid solution, water and brine, and dried over anhydrous sodium sulfate. The solvent is evaporated in vacuo, and the residue is washed with n-hexane to give 4-(3-chloro-4-methoxybenzylamino)-5-ethoxycarbonyl-2-methylthiopyrimidine (38.34 g).

(2) To a solution of the compound (5.00 g) obtained in the above (1) in chloroform (50 ml) is added a solution of m-chloroperbenzoic acid (4.00 g) in chloroform (50 ml) under ice-cooling, and the mixture is stirred for 2 hours. The reaction mixture is washed with a saturated aqueous sodium hydrogen carbonate solution and brine, and the organic layer is dried over anhydrous sodium sulfate, and the solvent is evaporated in vacuo to give crude 4-(3-chloro-4-methoxybenzylamino)-5-ethoxycarbonyl-2-methylsulfinylpyrimidine.

(3) The crude product obtained in the above (2) is dissolved in tetrahydrofuran (40 ml), and thereto is added a solution of L-prolinol (1.50 g) and triethylamine (1.60 g) in tetrahydrofuran (10 ml) at room temperature. The mixture is stirred overnight, and the reaction mixture is diluted with ethyl acetate, and washed with aqueous sodium hydrogen carbonate solution and brine. The organic layer is dried over anhydrous sodium sulfate, and the solvent is evaporated in vacuo. The residue is purified by silica gel column chromatography (solvent: chloroform) and crystallized from a mixture of ether and n-hexane to give (S)-4-(3-chloro-4-methoxybenzylamino)-5-ethoxycarbonyl-2-(2-hydroxymethyl-1-pyrrolidinyl)pyrimidine (4.72 g).

(4) A mixture of the compound (3.4 g) obtained in the above (3), a 10% aqueous sodium hydroxide solution (23 ml), and dimethylsulfoxide (34 ml) is stirred at room temperature for 15 hours. The reaction mixture is poured into a 10% aqueous citric acid solution, and the precipitates are crystallized from a mixture of tetrahydrofuran and ether to give (S)-4-(3-chloro-4-methoxybenzylamino)-5-carboxy-2-(2-hydroxymethyl-1-pyrrolidinyl)pyrimidine (2.52 g).

(5) A mixture of the compound (600 mg) obtained in the above (4), 2-aminomethylpyrimidine (217 mg), 1-(3-dimethylaminopropyl)-3-ethylcarbodiimide hydrochloride (323 mg), 1-hydroxybenzotriazole monohydrate (227 mg) and N,N-dimethylformamide (12 ml) is stirred at room temperature for 8 hours, and the reaction mixture is poured into aqueous sodium hydrogen carbonate solution. The mixture is extracted with ethyl acetate, washed with brine, and dried over anhydrous sodium sulfate. The solvent is evaporated in vacuo, and the residue is purified by silica gel column chromatography (solvent: chloroform:methanol=50:1) to give (S)-2-(2-hydroxymethyl-1-pyrrolidinyl)-4-(3-chloro-4-methoxybenzylamino)-5-[N-(2-pyrimidylmethyl)carbamoyl]pyrimidine (610 mg).

Preparations 2-4

The corresponding starting materials are treated in the same manner as described in Preparation 1 to give the compounds as listed in the following Table 1.

TABLE 1

| Preparation No. | ⌒A⌒N— | R⁰ | R¹ |
|---|---|---|---|
| 2 | imidazo-pyrimidine group | Cl | pyrimidinyl-methylamino |
| 3 | naphthyridine group | Cl | morpholinoethylamino |
| 4 | (S)-2-hydroxymethyl-1-methylpyrrolidinyl | Cl | pyrimidinyl-methylamino |

INDUSTRIAL APPLICABILITY

The present preparation for oral administration containing a PDEV inhibitor together with an acidic substance can achieve rapid dissolution of a medicinal substance in the digestive tract without being influenced by the conditions of the subject such as being suffering from anacidity or the time of administration such as just after eating, and can express the drug efficacy rapidly/immediately after administration, and hence is very useful in treatment of erectile dysfunction. Besides, according to the present oral preparation, even a medicinal substance, which becomes instable and/or hygroscopic when converted into an acid addition salt in order to improve the solubility, can be conveniently formulated in the free form. In addition, when a carbonate is compounded in addition to an acidic substance, the dissolution profile of a medicinal substance can be further improved, and the moldability in the preparation of tablets is also enhanced, which shows another advantage of the present invention.

The invention claimed is:

1. A preparation for oral administration comprising
   (A) as an active ingredient a compound (S)-2-(2-hydroxymethyl-1-pyrrolidinyl)-4-(3-chloro-4-methoxybenzylamino)-5-[N-(2-pyrimidinylmethyl)carbamoyl]pyrimidine in the free form; and
   (B) an organic acidic substance,
   wherein said compound is compounded with said organic acidic substance.

2. The preparation according to claim 1, wherein the organic acidic substance is selected from the group consisting of fumaric acid, tartaric acid, succinic acid, malic acid, ascorbic acid and aspartic acid.

3. The preparation according to claim 1, wherein the organic acidic substance is fumaric acid.

4. The preparation according to claim 1, wherein the compounding ratio of the compound and the organic acidic substance is in the range of 1:0.05 to 1:30.

5. The preparation according to claim 1, which further contains a carbonate.

6. The preparation according to claim 5, wherein the carbonate is one or more substances selected from the group consisting of alkali metal carbonates, alkali metal hydrogen carbonates and alkali earth metal carbonates.

7. The preparation according to claim 5, wherein the carbonate is calcium carbonate.

8. The preparation according to claim 5, wherein the content of a carbonate is 10 weight % or less of the total amount of the preparation.

9. The preparation according to claim 1, which is in the form of tablet.

10. A tablet which comprises
    (A) (S)-2-(2-hydroxymethyl-1-pyrrolidinyl)-4-(3-chloro-4-methoxybenzylamino)-5-[N-(2-pyrimidinylmethyl)carbamoyl]pyrimidine,
    (B) fumaric acid and
    (C) calcium carbonate.

* * * * *